Figure 1:
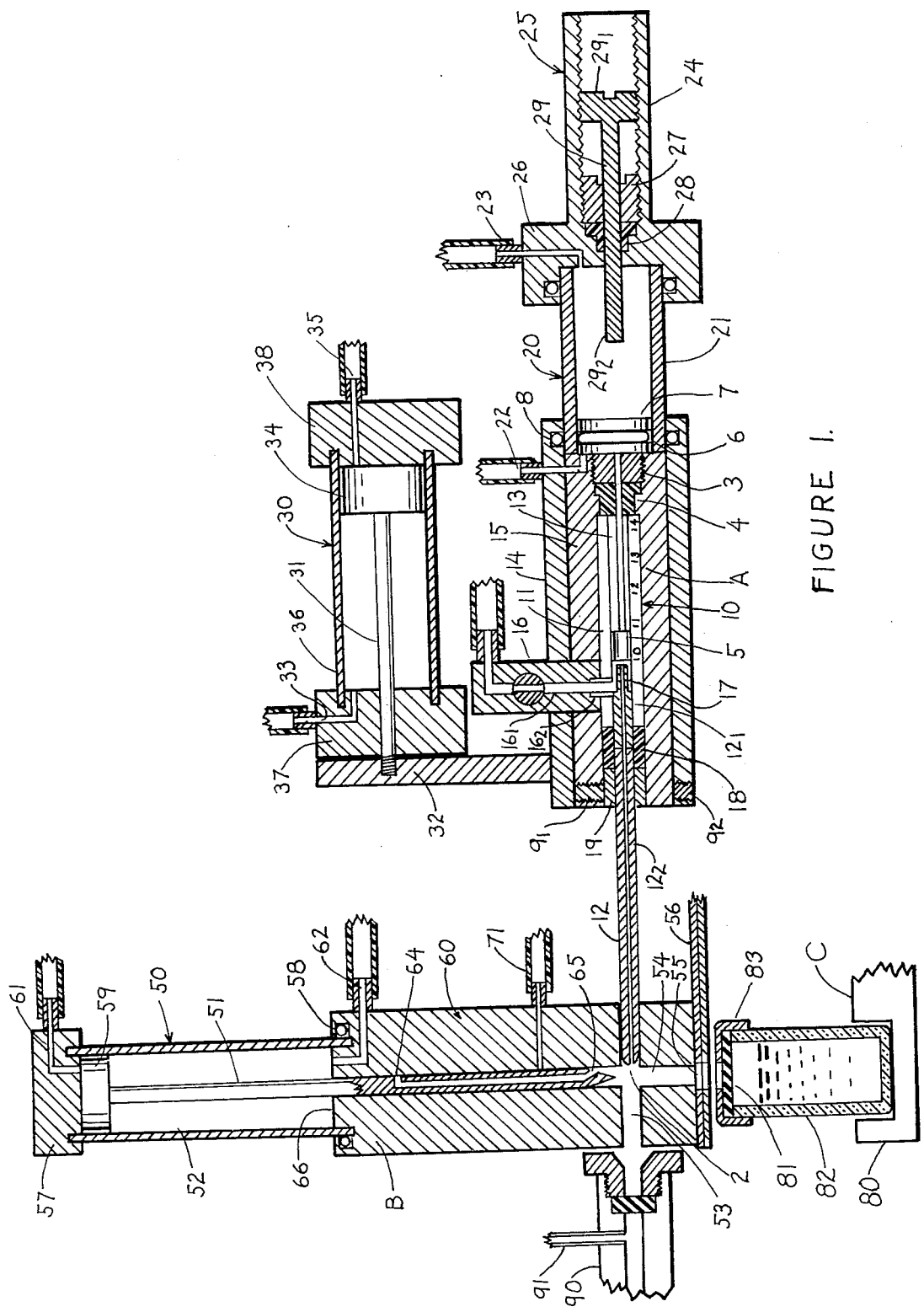

United States Patent [19]

Harris, Sr. et al.

[11] 3,940,995
[45] Mar. 2, 1976

[54] AUTOMATIC FLUID INJECTOR

[76] Inventors: Rano J. Harris, Sr., 1945 Carolyn Sue Drive; Rano J. Harris, Jr., 4423 S. Park Drive, both of Baton Rouge, La. 70815

[22] Filed: Sept. 9, 1974

[21] Appl. No.: 504,134

Related U.S. Application Data

[63] Continuation-in-part of Ser. No. 365,552, May 31, 1973, which is a continuation-in-part of Ser. No. 223,663, Feb. 4, 1972, Pat. No. 3,754,443.

[52] U.S. Cl. ............................. 73/422 GC; 73/423 A
[51] Int. Cl.² .................................................. G01N 1/14
[58] Field of Search ..................... 73/422 GC, 423 A

[56] References Cited
UNITED STATES PATENTS

| | | | |
|---|---|---|---|
| 3,754,443 | 8/1974 | Harris et al. | 73/423 A |
| 3,824,859 | 7/1974 | Harris et al. | 73/423 A |
| 3,841,160 | 10/1974 | Iwao | 73/423 A |

*Primary Examiner*—S. Clement Swisher
*Attorney, Agent, or Firm*—L. A. Proctor

[57] ABSTRACT

Am improved automatic fluid injector, or syringe, for accurately measuring and injecting quantities of fluid specimens, or samples, into various media, e.g., a receptacle or inlet of a modern analytical instrument, which includes the general combination of (a) an injector, or syringe assembly, inclusive of a needle syringe per se, (b) an injector feed assembly for automatically continuously purging, cleaning and filling the said syringe, and (c) a magazine, or feed tray, for transporting fluid specimen containing vials to the injector feed assembly for pick-up of the fluid specimen, and delivery to the syringe of the syringe assembly. Means are provided for movement of the syringe along a straight path for insertion and withdrawal of the needle from the inlet of the analytical instrument, and a reciprocable hollow probe, associated with the injector feed assembly picks up a fluid specimen from a fluid-containing vial delivered by the magazine or feed tray, and conveys the fluid to the syringe of the syringe assembly. The forward end of the barrel of the syringe is provided with a valved line through which an initial portion of the fluid specimen is passed to remove contaminants from previous specimens. An accurately measured portion of the fluid specimen is taken into the syringe by withdrawal of the plunger to a predetermined position, with the valved line in open or closed position; but the valve is closed prior to injection. The syringe is carried forward to insert the needle portion thereof through the inlet of the analytical instrument, the sample is then injected, and the needle then withdrawn. The several sub-assemblies are properly housed, and automatic controls provide for cyclically cleaning, purging, filling and injecting fluid specimens.

11 Claims, 8 Drawing Figures

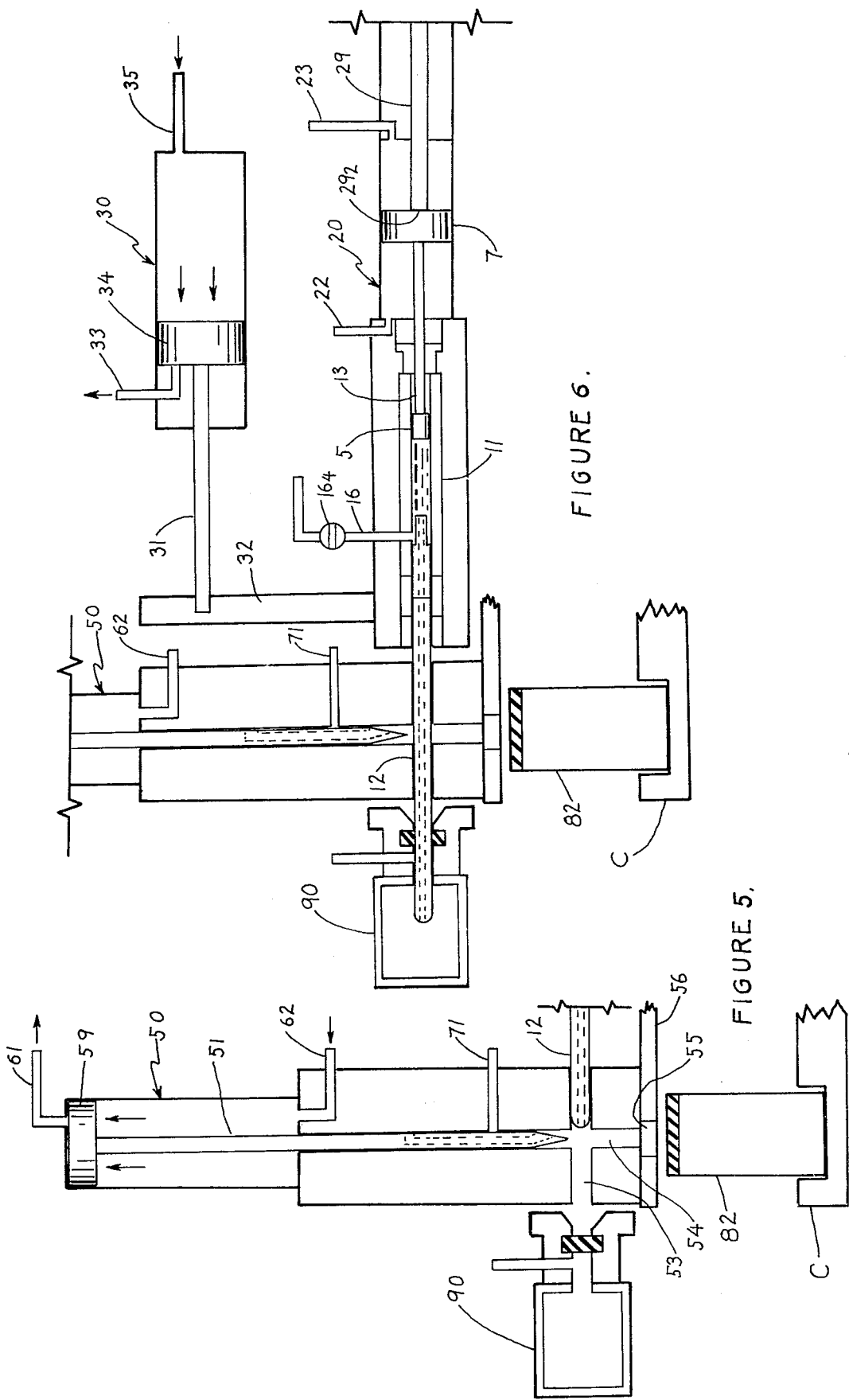

AUTOMATIC FLUID INJECTOR

REFERENCE TO RELATED APPLICATION

This application is a continuation-in-part of related U.S. Application Ser. No. 365,552, filed May 31, 1973, which in turn is a continuation-in-part of Application Ser. No. 223,663, filed Feb. 4, 1972 now U.S. Pat. No. 3,754,443, the disclosures of which are herewith referred to and fully incorporated by reference.

The present invention relates generally to automatic fluid injectors, or apparatus, for automatically measuring and injecting accurately measured quantities of fluids. More particularly, it relates to apparatus, especially fluid injection devices or syringes, for continuous automatic measurement and injection of very small, accurately measured quantities of gas and liquid specimens into various media, e.g., modern analytical instruments.

Fluid injection devices, particularly needle syringes, have gained wide acceptance by the industry, and by the scientific community, generally, for use in dispensing infinitesimally small, accurately measured fluid specimens, e.g., to modern analytical instruments such as mass spectrometers and gas chromatographs. Such syringes embody apparatus comprising a tubular body or barrel, on the forward end of which is fitted a hollow or tubular needle and, at the opposite end, a slidable plunger which travels within the bore of the barrel. Syringes of such character, and related devices, are capable of dispensing very small fluid specimens, accurately measured, on the order of a few microliters, or very small fractions of a microliter, e.g., from about 0.01 to about 5 microliters, or fractional parts thereof.

In recent years, due to the obvious advantages offered by the combination of automatic fluid injection instruments, and modern data gathering techniques, which greatly reduce operating manpower without decrease in accuracy, there is considerable demand for improved automated devices of these types.

It is, accordingly, a primary object of the present invention to provide new and novel fluid injectors readily adaptable to automatically perform the basic cyclic functions of purging and cleaning, filling, and injecting.

A particular object is to provide apparatus capable of continuously cyclically serially withdrawing precisely measured, infinitesimally small quantities of gas or liquid specimens from prefilled vials or containers, injecting the specimens in seriatim in reproducible quantities, and cleaning prior to subsequent withdrawal and injection of a subsequent specimen.

A further object is to provide apparatus of simple and relatively inexpensive construction, particularly apparatus which can be readily serviced and operated, which apparatus readily lends itself to rapid mass production techniques.

These objects and others are achieved in accordance with the present invention which embodies improvements in automatic fluid injector systems. A preferred type of automatic fluid injector is comprised generally of (a) an injector, or syringe assembly, inclusive of a needle syringe per se, (b) an injector feed assembly, or unit, for automatically purging, cleaning and filling the said syringe, and (c) a magazine, or feed tray, for transporting fluid specimen containing vials and positioning same in relation to the injector feed assembly for pick-up of the fluid specimen, and delivery to the syringe of the syringe assembly. The automatic fluid injector is provided with automation or control means for repetitively and automatically carrying out the functions of cleaning, purging and filling the syringe with predetermined quantities of fluid specimens, in timed sequence, and the several sub-assemblies of the automatic fluid injector are generally contained within a housing, or housings. The sub-assemblies constituting (a) the injector, or syringe assembly, inclusive of syringe, and (b) the injector feed assembly are preferably contained within a single housing below which is mounted (c) the magazine, or feed tray.

A reciprocable hollow probe, constituting a part of the injector feed assembly, serves as a conduit for pick-up of a fluid specimen from a vial delivered by the magazine or feed tray and transport thereof to the injector, or syringe assembly. Means are provided which pressurize the fluid contents of the vial after entry of the probe into the vial, and fluid contents therefrom are conveyed via a conduit portion of the probe to the injector, or syringe assembly.

The syringe of the injector, or syringe assembly, is provided with a valved side opening at the forward end of the barrel thereof at the location of "zero fill," or point forward, or flush with that reached by the forward face of the plunger on movement to its maximum forward position within the syringe barrel, as during an ejection stroke. The valved side opening, or line, is preferably located at the site of and enters into an annulus located about the base of the needle of the syringe slightly forward of the point of zero fill. On delivery of a fluid specimen from a vial, positioned for pick-up by the magazine or feed tray, the valved line is initially opened to allow the first portion of pressurized fluid specimen to pass through and clean the needle bore, said annulus and forward face of the plunger, such that contaminants, e.g., from a previous fluid specimen, can be discharged via the open valved line. With the valve in either open or closed position, the plunger is then withdrawn from the point of zero fill (or zero) to a desired preselected, or pre-determined location to permit ingress of an accurately measured quantitiy of the fluid specimen into the barrel of the syringe. The valve, if not previously closed, is now closed. The loaded syringe is then carried forward to insert the needle portion thereof through the inlet of an analytical instrument, the accurately measured quantity of the fluid specimen is then injected by forward movement of the plunger, and the needle is then withdrawn from the inlet.

The zero fill valved side opening, which constitutes a key and novel feature of the present invention, in the present combination, provides a number of advantages over the automatic fluid injectors disclosed and claimed in related Applications Ser. Nos. 365,552 and 223,663, supra. For example, the location of the side outlet opening at the point of zero fill considerably lessens the amount of contamination, e.g., as resultant from contamination by previous fluid specimens. Moreover, any contamination is far easier to remove, and less of the fluid specimen need be withdrawn from a vial for use in effecting the cleaning and purging step. Certain structural aspects of the automatic fluid injector itself are considerably simplified as contrasted with previous injectors, this lessening the costs of manufacture and maintenance. In fact, the actual number of steps requiring manipulation and movement of the plunger in the introduction of the fluid specimen into the analytical instrument is lessened.

The characteristics of preferred automatic fluid injectors, or syringes, and the principle of their operation, will be more fully understood by reference to the following detailed description of preferred embodiments, and to the attached drawings to which reference is made in the detailed description. Similar numbers are used to represent similar parts or components in different figures. A capital letter is used to designate a sub-assembly of the over-all combination.

Figure 8:
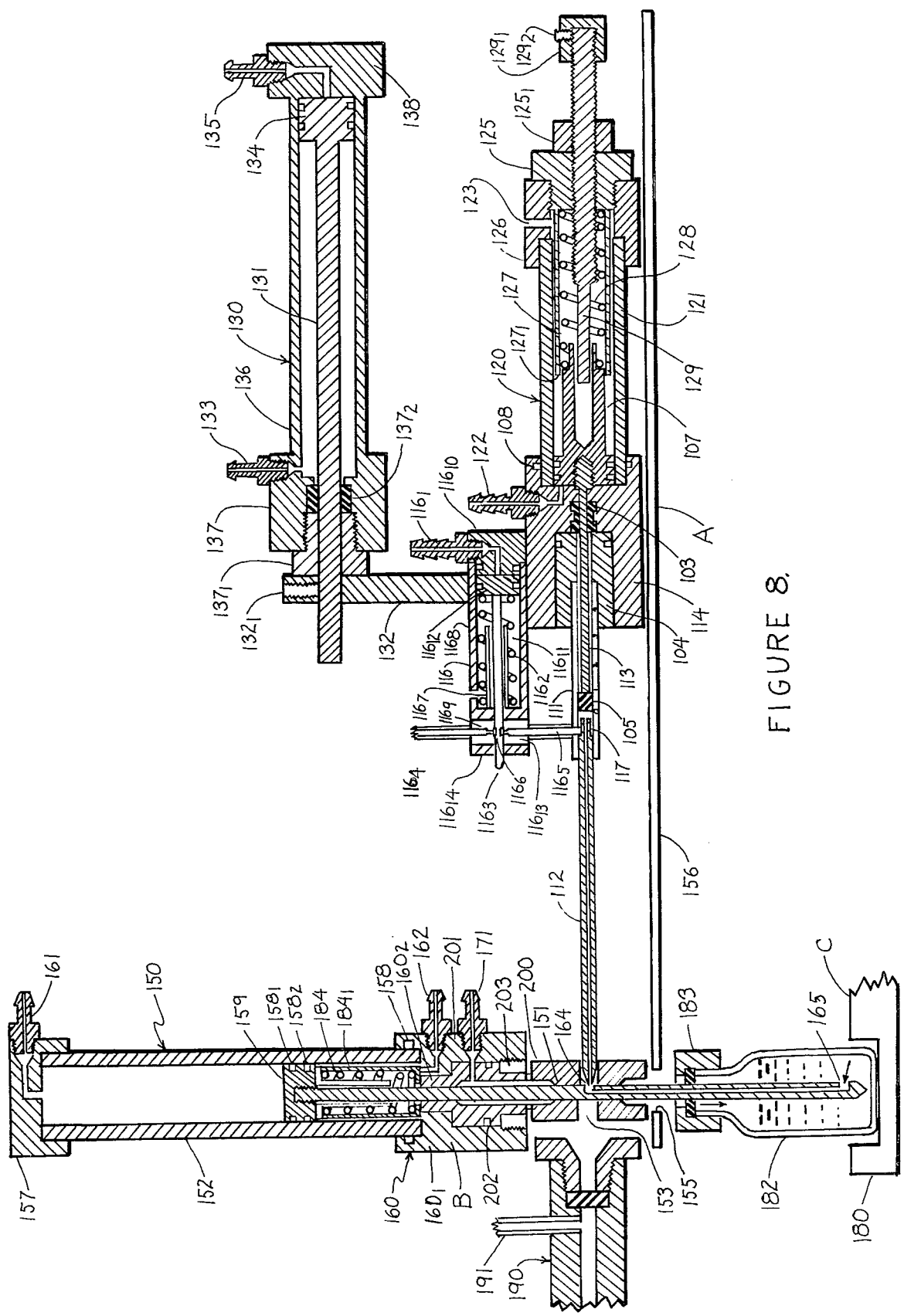

In the drawings:

FIGS. 1 and 8 are section views of preferred automatic fluid injectors, including an automated syringe, mounted on a plate, or housing, useful for positioning said syringe, in relation to an inlet, or medium, wherein an accurately measured fluid specimen is to be injected, the automatic fluid injector including, in combination, (a) an injector, syringe or syringe assembly, A, (b) an injector feed assembly, or assembly for supplying a fluid specimen to the syringe of the syringe assembly, B, and (c) a magazine or feed tray, C.

FIGS. 1 through 7 taken together describe a complete cycle of operation, i.e., they depict the complete sequence of sampling, trapping, measuring and injecting an accurately measured volume of a fluid specimen into a medium, e.g., an inlet to an analytical instrument. For clarity of illustration, FIGS. 2 through 7, many of which are fragmentary views of the over-all combination, are presented schematically.

Referring to FIG. 1, there is shown the principle components or sub-assemblies of an automatic fluid injector, according to a preferred form of the invention, this including the combination of (a) an injector, or syringe assembly A, (b) an injector feed assembly B, and (c) a magazine, or feed tray, C. These several units of the automatic fluid injector A,B,C are generally contained within a housing, or housings, and responsive to automatic control means such as described, e.g., by reference to Application Ser. No. 223,663, now U.S. Pat. No. 3,754,443. In brief compass, the principle features and over-all function of these several units are generally as follows:

a. The injector, or syringe assembly A, is comprised generally of a needle syringe 10, which includes the usual barrel 11, cannula or needle 12 mounted on the front end thereof, and plunger 13 mounted within several barrel 11. The plunger 13 is itself actuated by a double-acting cylinder piston unit 20, adjacent to and forming an integral part of needle syringe assembly A. The syringe assembly A, inclusive of the double-acting cylinder piston unit 20, is mounted and carried on the forward end of a piston 31 of a double-acting cylinder piston unit 30, also a part of the overall syringe assembly A, and reciprocable therewith for movement of the syringe 10 along a straight path in alignment with, e.g., a septum inlet 90;

b. the injector feed assembly B, the function of which is to provide a fluid specimen for the syringe 10, is comprised generally of a double-acting cylinder piston unit 50, the piston 51 thereof being a reciprocable hollow probe associated with means which enable said probe to be projected into a source of a fluid specimen to act as a conduit for receipt and transfer of the fluid specimen which is supplied thereto under a slight pressure, which acts as a driving force, to fill the syringe 10; and c. a magazine, or feed tray C, for transporting vials which contain fluid specimens to a location for pick-up by the probe 51 for delivery to the syringe 10. A preferred type of feed tray C is described by reference to U.S. Pat. No. 3,754,443. These several sub-assemblies A,B,C, and their function, are explicitly described in the following paragraphs.

The syringe 10 of the overall needle syringe assembly A consists generally of a pair of contiguous tubular members comprising a relatively large diameter rearward section 21, which constitutes the barrel portion of double-acting cylinder piston unit 20, and a smaller diameter forward section 11, constituting the barrel of the syringe. The barrel 11, generally constituted of clear plastic or glass with indicia marks scribed thereon, is located within a large outer tubular member 14 and a tubular member 15 of intermediate diameter, the members 11,14,15 being concentrically mounted one as regards the other. The barrel 11 is provided with a valved side opening or vent line 16 through which the forward end of the barrel 11 can be opened or closed. It will thus be observed that an annulus 17 at the base of the needle 12 is directly communicated to an end of the tubular segment $16_1$ which is fitted through a tubular seal $16_2$ located within an opening through the side wall of barrel 11. The needle 12 is provided with an easily changeable forward portion $12_2$ and a base portion $12_1$, segments $12_1,12_2$ being abutted together and the bores thereof being communicated one segment with the other at a location inside a tightly fitting tubular seal 18. The seal 18 and the syringe 10 are held in place within the intermediate tubular member 15 by a gland 19 which is secured in place via a screw $9_1$, or easily removed for changing out the seal 18 and syringe 10. The tubular member 15 is retained in place by means of screw $9_2$.

The intermediate tubular element, or sleeve 15, can also be removed from the larger outer tubular element 14, if desired, by first removing the valved vent line 16. In place, however, the outer tubular element 14 is fitted snugly upon the forward end of the smaller diameter tubular element 21, which constitutes a portion of the double acting cylinder piston unit 20, these members being hermetically insulated one from the other via O-ring seal 8. The plunger 13, it will be observed, is provided with a cylindrical shaped grooved head 7, the grooved portion of which contains an O-ring seal 6. The forward end of plunger 13 is also provided with a seal 5, constructed of resilient material, preferably Teflon, formed, e.g., as described in U.S. Pat. No. 3,577,850 herewith incorporated by reference. The stem portion thereof is also fitted through a tubular seal 4 held in fixed position rearward of the barrel 11 by an externally threaded tubular member or retaining ring 3.

The rearward section of the syringe, constituting the double acting cylinder-piston unit 20, is provided with an air inlet-outlet 22 leading into the forward end of the chamber and an air inlet-outlet 23 leading into the rearward end of the chamber, each being provided with flexible hose connections as is the vent line 16. The piston 13 can thus be reciprocated within the barrel 11 via alternate injection of air or other fluid into inlet-outlets 22,23, the enlarged piston head 7 being hermetically sealed and isolated from barrel 11.

In a preferred embodiment, a plunger stop assembly 25, of adjustable character, is located at the rearward end of the chamber of cylinder piston unit 20 and within the path of travel of the piston 13. The function of the plunger stop assembly 25 is to permit piston 13 to traverse a predetermined, or pre-set, length of the chamber of double-acting cylinder piston unit 20. It can be constructed in similar manner to those described by reference to any of Applications Ser. No. 365,552 or Ser. No. 223,663 (now U.S. Pat. No. 3,754,443), supra, or Application Ser. No. 333,120, also incorporated by reference.

A preferred type of plunger stop assembly 25 is constituted of an open end tubular member 24 which forms a portion of, or is integrated with, the cylindrical shaped end wall 26 forming the rearward portion of the chamber of the double-acting cylinder piston unit 20. The inside diameter of tubular member 24 is threaded for receipt and threadable engagement with an externally threaded tubular member or gland 27 which tightens down and secures the tubular packing 28 in place at the forward end of tubular member 24, and within its seating within the rearward face of end wall 26. A shaft 29, provided with an externally threaded enlarged head $29_1$, is projected through the gland 29 and tubular packing 28, is threadably engaged with the internal threads of tubular member 24, and is axially movable within the tubular member 24. It will be particularly observed that the forward end $29_2$ of shaft 29 is moved forwardly or rearwardly within the chamber formed within wall 11 of the cylinder-piston unit 20 by adjustment of shaft 29 which is rotatably mounted within the tubular member 24. The shaft 29, preferably provided with a notched head $29_1$ for ease of adjustment, is movable along the axis of the tube 24 on rotation of the shaft 29 such that the distance which the shaft 29 is free to traverse can be adjusted or preselected. It will thus be observed that the distance between the rearward face of piston head 7 and the forward end $29_2$ of shaft 29, as well as the thickness of piston head 7 of piston 11, determine the distance of travel of plunger 13 within the chamber of the smaller diameter forward section 11 of the syringe 10, and that such distance can be readily set by rotation of shaft 29 which lengthens or shortens the distance between the forward face of head 7 and the rearward end of shaft $29_1$. It will be observed that the plunger 13 is reciprocated within the pre-set limits by injection of air via inlet-outlet line 22 into the forward side of the cylinder piston unit 20 to drive the piston 13 rearward, and by injection of air via inlet-outlet line 23 into the rearward side of the cylinder-piston unit 20 to move piston 13 forwardly.

The smaller diameter tubular forward section 11 of the syringe 10 is generally constructed of transparent plastic or glass, and optionally scribed ith indicia representative of the internal volume. The volume of the chamber formed within the tubular barrel 11 is exaggerated in the drawings for clarity and, of course, can be varied in size depending upon the volume of specimen to be accurately measured and delivered, e.g., as where the specimen is a liquid or gas. One method of varying the volume of the chamber within barrel 11 is by adjustment of the length of stroke of the plunger, as suggested via adjustment of the plunger stop assembly 25. A cannula or needle 12 is fixed within the forward wall or upon the forward end of the barrel 11 by various means well known to the art. The needle 12 can thus be snugly fitted into the forward end of the barrel or smaller diameter tubular forward section 11 through an opening made in the forward wall, and an air-tight seal provided about the annulus between the outer wall of the needle 12 and the wall of the barrel 11. The needle 12, provided with a forward opening 2, is extendable through horizontal opening 53 of the housing 60, and is communicable, in proper position, with the vertical opening 54 via their intersection (or communicating channel).

The syringe assembly A is, in its entirety, affixed via a mounting bracket 32 on the forward end of piston 31 of the double-acting cylinder-piston unit 30, which can be secured via mounting brackets (not shown) upon the wall of a housing (not shown). The double-acting cylinder piston unit 30 thus includes the usual hollow air-tight casing (or enclosing wall) 36, with enclosing end walls 37,38, and air inlet-outlet openings 33,35. The syringe assembly A, inclusive of syringe 10, is reciprocably movable along a fixed horizontal path via reciprocation of plunger 31. Forward movement of the piston 31 is accomplished by injection of fluid (e.g., air) into the rearward end of the cylinder-piston unit 30 via inlet 35, the fluid impinging upon the rearward face of piston head 34 of piston 31 causing the entire syringe assembly A, inclusive of syringe 10, to be thrust forward, this causing passage of the needle 12 through the opening 53 of housing 60, this producing insertion of the dispersing end of the needle 12 through a septum or other type of inlet as for sample injection in a modern analytical instrument. Rearward movement of the piston 31 by injection of fluid (e.g., air) into the forward end of the unit via inlet 33 impinges upon the forward face of piston head 34 to move the syringe 10 in the opposite direction, this causing withdrawal of the needle 12 from the sample inlet 90.

The injector feed assembly B comprises a double-acting cylinder-piston unit 50, inclusive of a piston or probe 51, the forward portion of which is mounted and reciprocable within a tubular shaped housing 60. The probe 51 is hollow or tubular, at least in part, to serve as a conduit for receipt and transfer of a fluid specimen, supplied thereto by pressurizing means described hereafter, to fill the syringe 10. In the embodiment described by reference to FIG. 1, and associated figures, the injector feed assembly B is vertically oriented, as contrasted with the orientation of the syringe assembly A which can be horizontally or vertically oriented. The double-acting cylinder-piston unit 50 and tubular housing 60 are contiguous and can be fabricated as a unitized assembly, and mounted within a main housing (not shown) via appropriate fastening means. It will be observed, in general, that the probe 51 is reciprocable and can be moved or projected downwardly through the complete length of the axial opening 54 of tubular housing 60, through the opening 55 of a mounting plate 56 of a housing (not shown), for penetration of the septum 81 of a specimen filled vial 82. The probe 51 is provided with openings 64,65 to enhance its utility to serve as a conduit for pick-up and transfer of fluid, and means are provided for pressurizing the fluid contents of the vial 82 so that fluid from a vial 82 can be picked up by the probe 51 and conveyed upwardly for delivery to the syringe 10.

The double-acting cylinder-piston unit 50, like double-acting cylinder-piston unit 30, also includes an enclosing side wall 52, an enclosing upper end wall 57, and an enclosing lower end wall 66 formed by the upper face of tubular housing 60. An O-ring 58 is provided to more effectively seal the lower end of the unit 50 and air inlet-outlet openings 61,62 are provided for reciprocation of probe 51, via alternate impingement of air on the opposite faces of piston head 59.

The double-acting cylinder-piston unit 50, like double-acting cylinder-piston units 20,30, is generally pneumatic, air being used as the driving medium. Virtually any source of pressurized fluid, e.g., hydraulic fluid or pneumatic pressure, however, can be used to actuate this or any other of the cylinder-piston units. Or, on the other hand, the cylinder-piston units can be spring actuated, or actuated by various other means known in the art. The probe 51 of cylinder-piston unit 50 can thus be moved upwardly via pressurized fluid injected via gas inlet-outlet port 62, and downwardly by injection of pressurized fluid injected via gas inlet-outlet port 61. When the piston 51 is thrust to its extreme downward position, by fluid pressure acting against the upper face of piston head 59, the lower terminal end of the probe 51 is projected through the opening 55 in the wall 56 of the lower housing, through a centrally located opening through a septum cap 81 of a vial 82 for pick-up of a fluid specimen, delivered into position by action of a feed tray or magazine 80.

In the several embodiments of this invention, a magazine or feed tray 80 is provided for conveying fluid specimen-containing vials 82 in seriatim to a location beneath the opening 55 or housing 56 for pick-up by the probe 51. The vials 82 are suitably of open screw top type, sealed with an elastomer septum 81 to prevent leakage or contamination and to permit pressurization. As the vials 82 are moved into position beneath the opening 55, the probe 51 can be moved downwardly and projected through the opening 55 at the bottom of housing 56 to pass through the open caps and penetrate the septum of the vials 82 for pick-up of the fluid specimen.

Figure 2:
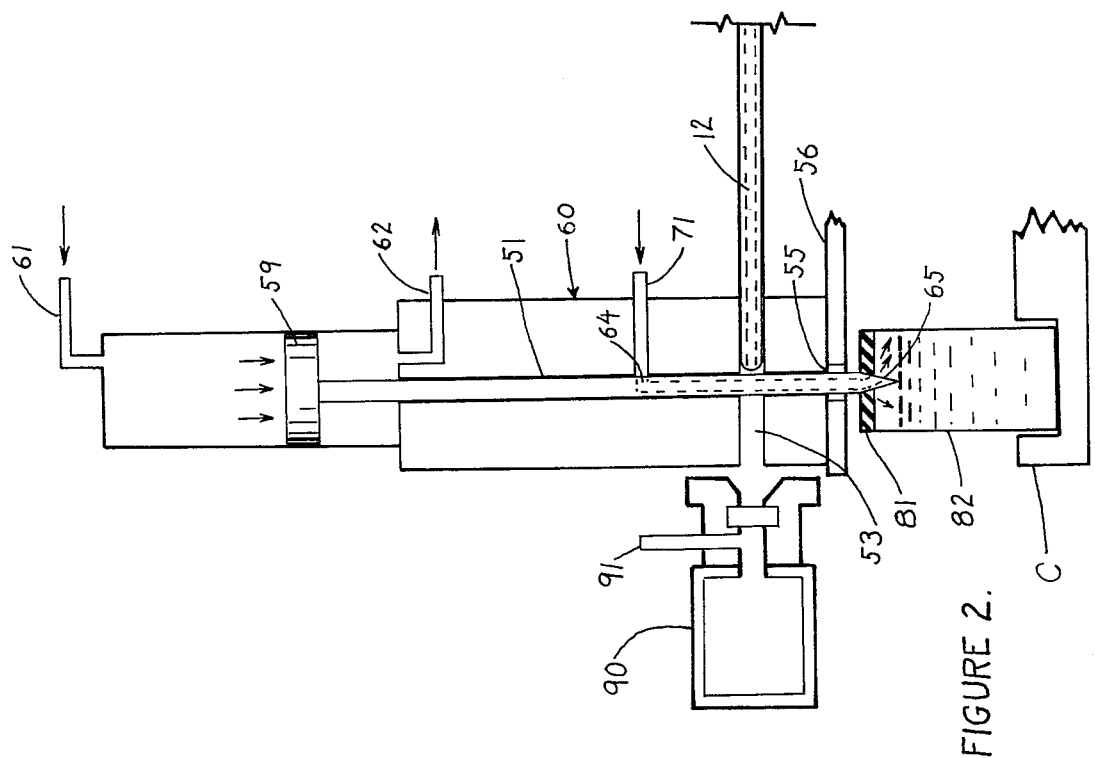
Figures 3, 4:
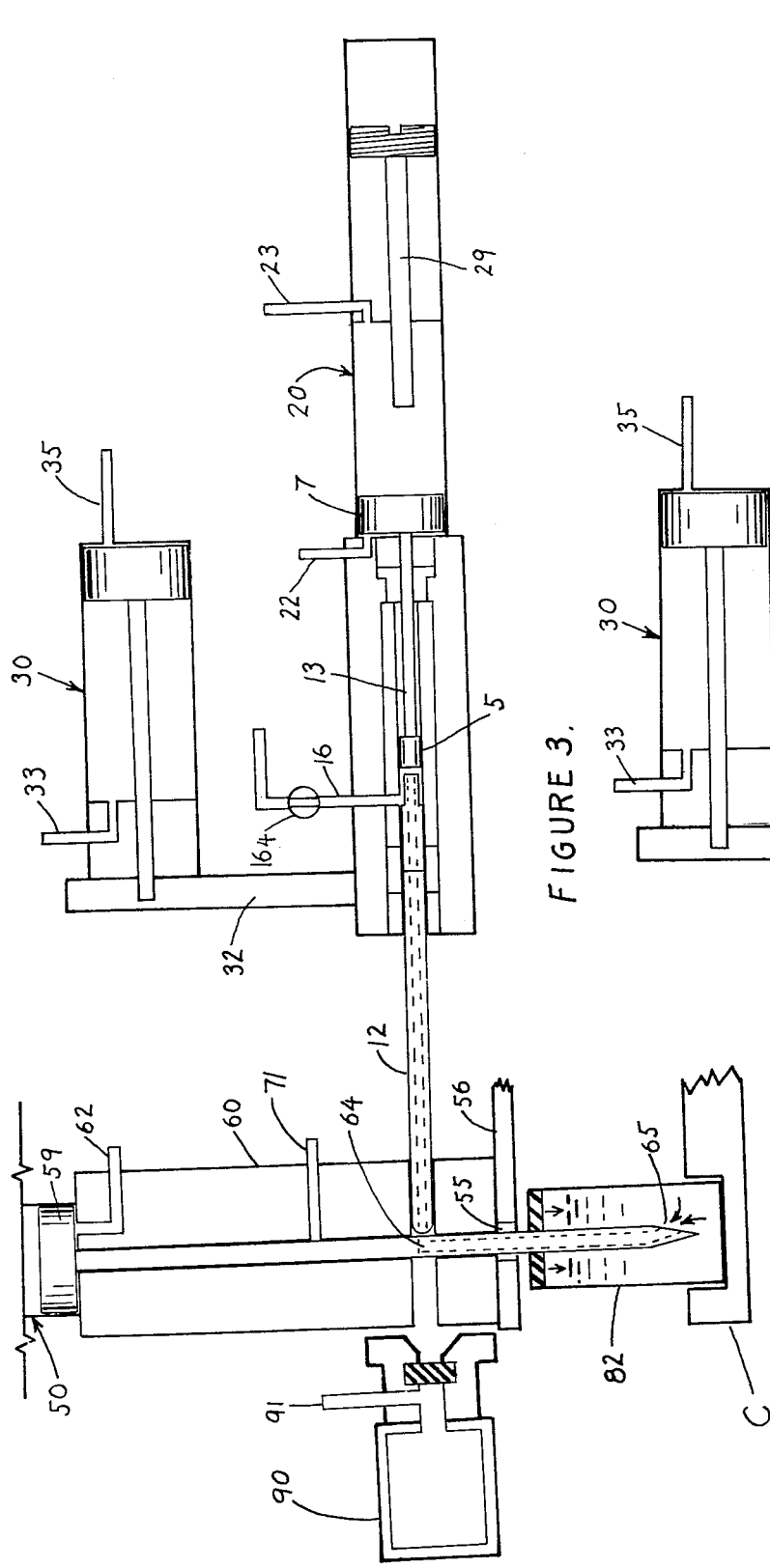
Figure 7:
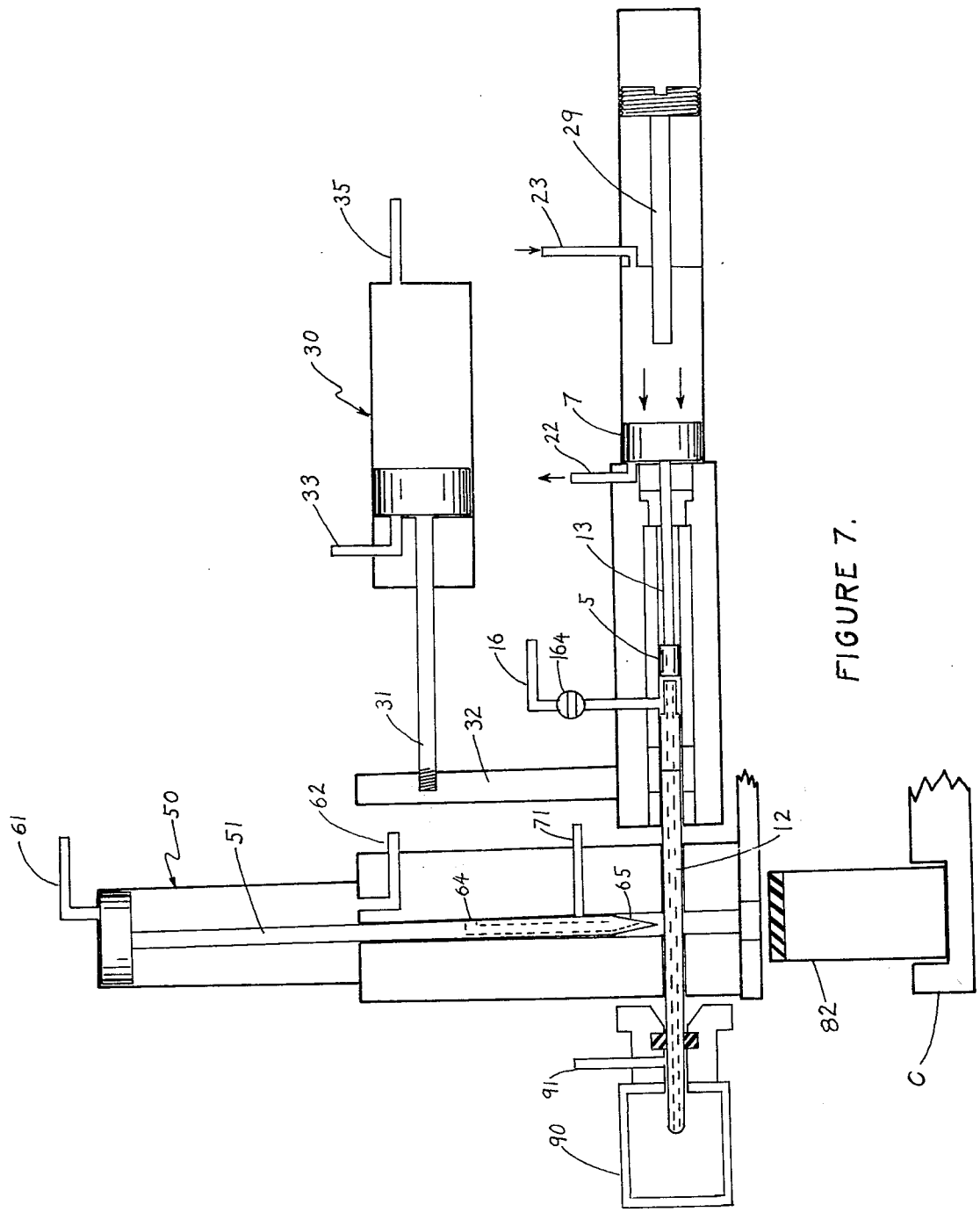

An operating cycle is described by reference to FIG. 1 and by reference to the several schematic FIGS. 2 through 7, these figures depicting a series of views describing the filling, injecting, cleaning and purging of syringe 10. The time sequence can be repeated ad infinitum, as follows:

a. Referring first to FIG. 2, probe 51 is pushed downwardly from an upward starting position (FIG. 1) by pressurized air which enters into the chamber of the cylinder-piston unit 50 via the inlet-outlet port 61 to impinge on piston head 59. Simultaneously, air is exhausted via air inlet-outlet port 62. The forward portion of probe 51 is hollow and openings 64,65 are communicated one with the other by the axial opening through the probe. The septum 81 of the air-tight vial 82 (located as shown in FIG. 1 between a threaded cap 83 and the upper shoulder of the glass vial 82) is penetrated by the sharp, or pointed, end of the probe 51. As the upper side vent opening 64 passes the pressure gas inlet 71, gas enters into side vent opening 64 and flows downwardly through the axial opening through hollow probe 51 to exit via the lower opening 65 and into the vial 82, pressurizing the latter.

b. Referring now to FIG. 3, prior to the time that probe 51 has reached its most downward position, the gas inlet 71 no longer remains open to the upper side vent opening 64 of the probe 51. However, the pressure remains within the vial 82, and the upper side vent opening 64 of the probe 51, at the maximum downward position of piston 51, is now open to the axial opening at the dispensing end of needle 12. At this point in time, pressurized fluid specimen from vial 82 flows through the opening 65 and into the axial opening through probe 51 and into the needle 12. The fluid specimen, the initial charge of which acts as a purge to eliminate contamination from previous specimens, then passes through the bore of needle 12, enters the annular opening 17 at the base of the needle, forward of the tip 5 of plunger 13, and exists via line 16 and valve $16_4$, now in open position. On termination of the downward movement of probe 51, it will be noted that inlet-outlet port 62 is in fully vented position.

c. Reference is now made to FIG. 4 of the drawings. Valve $16_4$ is now closed, liquid no longer being allowed egress via line 16. Air is injected via inlet-outlet line 22 into the forward side of cylinder-piston unit 20, the air impinging upon piston head 7 of plunger 13, moving plunger 13 rearwardly. Fluid specimen is withdrawn through the dispensing end 2 of needle 12, entering and filling the chamber formed by wall 11, or barrel of the syringe, as the tip 5 of plunger 13 retreats rearwardly. The volume of fluid specimen trapped within the barrel of the syringe is predetermined by the preselected distance of rearward movement of plunger 13, the rearward movement of which ceases as the rearward face of piston head 7 impinges upon the forward terminal end $29_2$ of adjustable shaft 29.

d. Referring to FIG. 5, the probe 51 is next moved away from its position blocking horizontal opening 53, to permit passage of needle 12 (i.e., in embodiments wherein probe 51 and needle 12 are aligned in the same plane). Probe 51 is thus lifted clear of opening 53 by injection of air into inlet-outlet opening 62 61 is vented, air impinging upon the under face of plunger head 59 moving probe 51 upwardly. The injector feed assembly B of the automatic fluid injector is thus now repositioned as shown by reference to FIG. 1, the syringe 10 now having been purged of contaminants and filled with a fresh fluid specimen which is to be injected into inlet 90.

e. In order to effect the desired injection of the fluid specimen into septum inlet 90, the entire syringe 10, as shown by reference to FIG. 6, is now moved forward by air injected via inlet-outlet line 35 into cylinder-piston unit 30, while inlet-outlet line 33 is in vented position, the air impinging upon the piston head 34, causing the piston 31 to be thrust forwardly thereby causing the needle 12 to be inserted into inlet 90 of an analytical instrument, e.g., a gas chromatograph.

f. Referring to FIG. 7, the manner of actual injection of the fluid specimen is shown. Air to inlet-outlet port 23 thus impinges against the rearward face of piston head 7 to drive plunger 13 to its extreme forward position, the forward end 5 thereof transversing the pre-set length of the chamber to inject the fluid specimen into the inlet 90. Carrier gas is admitted via line 91 to aid in the injection of the fluid specimen into inlet 90.

g. The entire syringe assembly A is next repositioned by injection of air into inlet-outlet port 33, of cylinder-piston unit 30, while inlet-outlet port 35 is vented. The entire syringe assembly A is thus repositioned as shown by reference to FIG. 1.

Referring to FIG. 8, there is shown a preferred production model of the instrument heretofore described. This model, like that described in FIG. 1, includes the same sub-assemblies A,B,C which do not differ in principle, function or operation from that already described, but does contain features which provide more effective and efficient operation, as well as easier maintenance and construction.

The syringe assembly A of the preferred production model, like the syringe assembly A described by reference to FIG. 1, includes generally also a needle syringe 120 mounted upon a double-acting cylinder-piston unit 130. The syringe per se, like that previously described, is characterized by the usual barrel 111, forward mounted needle 12, and rearwardly located plunger 113 mounted within the barrel 111. The plunger 113 thereof is actuated by a double-acting cylinder piston unit adjacent to and forming an integral part of the overall syringe assembly. Syringe assembly 120 is carried on the forward end of piston 131 of cylinder piston unit 130, an integral portion of sub-assembly A, the syringe assembly 120 being reciprocable therewith for movement of the syringe along a straight path in alignment with, e.g., septum inlet 190.

The syringe per se of sub-assembly A comprises contiguous tubular members inclusive of barrel 111 concentrically mounted within tubular members 104,114 adjoined to the rearward tubular member 121. The barrel 111 is thus hermetically sealed inside intermediate tubular 104 which, in turn, is contained within outer tubular member 114; and tubular member 121 is, in turn, concentrically mounted and hermetically sealed via O-ring seal 108 within the rearward side of tubular member 114. Plunger 113, the forward end of which is reciprocable within barrel 111 and the rearward end of which is reciprocable within tubular member 121, is mounted within a seal 103 which hermetically isolates the barrel 111 from the chamber within the confines of tubular member 121. The barrel 111 and plunger 113, inclusive of plunger tip 105, are essentially as characterized with reference to the instrument described in FIG. 1. The head 107 of plunger 113 is tubular shaped to provide better stability, the end of shaft 129 being fitted within the axial opening therethrough to guide the plunger 113 as it is reciprocated.

The rearward portion of syringe assembly 120 also comprises a double-acting cylinder piston unit and plunger stop assembly. The double-acting cylinder piston unit is this instance includes only a single pneumatic drive means, the plunger in its movement compressing a helical shaped compressible spring which returns it to its original position at the desired point in time. The rearward section of the enclosing wall 121 is thus closed by means of an internally threaded tubular element 126, provided with an exhaust port 123, within which is mounted the internally and externally threaded tubular member 125 which in turn contains externally threaded shaft 129. The tubular member 125, which is threadably engaged to the member 126 provides a forward tubular section within which a helical spring 128 is seated. The member 126 is hermetically sealed upon the end of tubular member 121, and the member 125 is in turn retained in place adjacent to member 126 via a locking nut $125_1$. The shaft 129, conveniently provided with a knobbed end $129_1$ retained in place via a set screw $129_2$, is axially movable backward or forward within the chamber formed within the confines of tubular member 121 by rotation of shaft 129. The rearward section of the syringe, constituting the double acting cylinder-piston unit, is provided with an air inlet-outlet 122 leading into the forward end of the chamber within the confines of tubular member 121, and with a flexible hose connection through which a fluid, e.g., air, can be injected to drive the plunger 113 rearwardly against helical spring 128 seated within the tubular member 127. The plunger 113 can thus be reciprocated within the barrel 111 via injection of air or other fluid into inlet-outlet 122, the plunger head 107 being hermetically sealed and isolated from barrel 111. In the rearward movement of the plunger, ambient air egresses via exhaust port 123.

The shaft 129 of the plunger stop assembly is located at the rearward end of the chamber of cylinder piston unit and within the path of travel of the plunger 113. The function of the plunger stop assembly is to permit plunger 113 to traverse a predetermined, or pre-set, length of the chamber of the double-acting cylinder piston unit, which function has been described by reference to FIGS. 1 through 7.

Whereas valves, or valve means, of various known types can be used for opening and closing the outlet located at the forward end of the barrel of the syringe in response to automated signals, in properly timed sequence, a preferred type of pneumatically actuated valve 116 of the cylinder-piston type is described by continued reference to FIG. 8. Valve 116 is, in effect, a compartmented tubular member. A first compartment of valve 116 is constituted by enclosing side and end walls $116_8$, $116_9$, $116_{10}$. The latter, or rearward wall $116_{10}$ is hermetically sealed within the tubular side wall $116_8$ and provided with a gas, or fluid inlet $116_1$. A tubular guide $116_7$ is mounted on the forward wall $116_9$ and a helical spring $116_2$ of somewhat larger diameter is fitted thereover and seated between the external face of said guide member $116_7$ and the inside face of side wall $116_8$. An opening is provided within the forward wall $116_9$ and a piston or stem $116_{11}$, having an enlarged rearward cylindrical shaped head $116_{12}$, is fitted therethrough. The forward portion of the piston $116_{11}$ is is circumferentially grooved, slotted or perforated, e.g., by a continuous circumferential slot $116_6$, and this portion of the piston is fitted through a tubular packing $116_{13}$ contained within the second compartment, or compartment located between forward wall $116_9$ of the cylinder piston unit and wall $116_{14}$.

The axial opening through the tubular packing $116_{13}$, at one side, is communicated via line $116_5$ with the inside of syringe barrel 111 and, on the other side, is communicated with a sump (not shown) via line $116_4$. It will be observed that, in the position shown, fluid specimen can be transferred from the annular opening 117 at the base of needle 112 through the slotted opening $116_6$ and line $116_4$. Egress of the fluid specimen from the annulus 117, on the one hand, can be interrupted and valve 116 closed by pressurized fluid transmitted via inlet $116_1$, the fluid impinging on head $116_{12}$ of the piston $116_{11}$ displacing it forwardly to misalign the slot $116_6$ of the piston $116_{11}$ with the axial opening through the tubular packing $116_{13}$. On release of the pressure, on the other hand, the piston $116_{11}$ is returned to the position shown in the figure by re-extension of the previously compressed spring $116_2$.

The syringe assembly, like that described by reference to FIG. 1, is affixed on a mounting bracket 132 on the forward end of piston 131 of the double-acting cylinder-piston unit 130, which can be secured via mounting brackets (not shown) upon the wall of a housing (not shown). The double-acting cylinder piston unit 130 includes the usual hollow air-tight casing (or enclosing wall) 136, with enclosing end walls 137,138, and air inlet-outlet openings 133,135. The syringe assembly is reciprocably movable along a fixed horizontal path via reciprocation of plunger 131, forward movement of which is accomplished by injection of fluid (e.g., air) into the rearward end of the cylinder-piston unit 130 via inlet-outlet 135, the fluid impinging upon the rearward face of piston head 134 of piston 131 causing the entire syringe assembly to be thrust forward, this causing passage of the needle 112 through the opening 153 of lower housing 200, this producing inserting of the dispersing end of the needle 112 through the septum of septum inlet 190. Rearward movement of the piston 131 by injection of fluid (e.g., air) into the forward end of the unit via inlet 133 impinges upon the forward face of piston head 134 to move the syringe in the opposite direction, this causing withdrawal of the needle 112 from the sample inlet 190. Unlike the device described by reference to FIG. 1, however, the piston 131 is sealed within the cylinder formed by enclosing side wall 136, rear wall 138 and forward wall 137 via a tubular packing $137_2$ retained in place by an externally threaded tubular member $137_1$, the forward end of the piston 131 being extended through said members 137, $137_1, 137_2$ for retention thereon of mounted bracket 132 held via a set screw $132_1$.

The injector feed assembly B of the improved production model comprises a double-acting cylinder-piston unit 150, inclusive of a piston or probe 151, the forward portion of which is mounted and reciprocable within an upper tubular housing 160 and a contiguously mounted lower tubular shaped housing 200. The probe 151 is hollow or tubular, at least on its lower end, to serve as a conduit for receipt and transfer of a fluid specimen, supplied thereto for filling the barrel 111 of the syringe. The double-acting cylinder-piston unit 150 and contiguous tubular housings 160, 200 can be fabricated as a unitized assembly, and mounted within a main housing (not shown) via appropriate fastening means. The probe 151 is reciprocable and can be moved or projected downwardly through the complete length of the axial openings through tubular housings 160, 200, and through the opening 155 of a mounting plate 156 of a housing (not shown), for penetration of the septum of a specimen filled vial 182. The probe 151 is provided with openings 164, 165 to enhance its utility to serve as a conduit for pick-up and transfer of fluid, and can provide means for aiding in pressurizing the fluid contents of the vial 182 so that fluid from vial 182 can be picked up by the probe 151 and conveyed upwardly for delivery to the syringe.

Double-acting cylinder-piston unit 150, in brief compass, is formed by an enclosing side wall 152, an enclosing upper end wall 157, and an enclosing lower end wall 166 formed by the upper face of upper tubular housing 160. An O-ring 158 hermetically seals the lower end of the unit 150 and air inlet-outlet openings 161, 162 are provided for reciprocation of probe 151, via alternate injection of air on the opposite faces of piston head 159. A buffer assembly, comprised of a helical spring 184 mounted within a tubular guide member $184_1$, is located within the bottom of cylinder piston unit 150 to slow the descent and for suppression of any shock which might otherwise be caused by descent of the probe 151 and its impingement against the bottom of cylinder 152.

The upper housing 160 is of tubular design and contains, besides inlet-outlet 162, a gas inlet 171 through which gas can be injected to pressurize vial 182. The tubular housing 160 is thus comprised of outer and inner concentrically mounted cylindrical members $160_1, 160_2$, the inner member $160_2$ containing an enlarged axial opening along its lower extremity into which air or other gas can be injected via gas inlet 171 to pressurize the vial 182. The inner tubular member $160_2$, which is hermetically sealed with the outer tubular member $160_1$ via O-ring seal 202, is retained in place via a ring gland member 203. The tubular housing 160 is thus comprised of outer and inner concentrically mounted cylindrical members $160_1, 160_2$, the inner member $160_2$ containing an enlarged axial opening along its lower extremity into which air or other gas can be injected via gas inlet 171 to pressurize the vial 182. The inner tubular member $160_2$, which is hermetically sealed with the outer tubular member $160_1$ via O-ring seal 202, is retained in place via a ring gland member 203. The tubular housing 160 is tightly fitted against the lower tubular housing 200 which rests upon the wall 156, the axial openings of the housings 160, 200 being aligned with opening 155 within wall 156. In an operating cycle, the probe 151 can be raised, elevated, or moved upwardly via pressurized fluid injected via gas inlet-outlet port 162, or pushed downwardly by pressurized fluid injected via gas inlet-outlet port 161. When the piston 151 is thrust downwardly, the vial 182 can be pressurized by injection of air into inlet 171, the air entering the chamber of housing 160, port 164 on passage, and exiting via port 165 into the vial 182 as occurs after the lower terminal end of the probe 151 has been projected through the opening 155, through wall 156 of the lower housing 200, and through a centrally located opening of a septum cap 183 of vial 182. And thereafter, as when the probe 151 has reached its extreme downward postion as shown by reference to the figure, pressurized fluid specimen can be delivered via the axial opening of the probe 151 through the needle 122, initially for cleaning the annulus 117 as when valve 116 is opened to permit egress of contaminated fluid and subsequently, upon closure of valve 116 and withdrawal of plunger 113, for filling the syringe with an accurately measured quantity of the fluid specimen for delivery to septum 190. An operating sequence for this device is substantially as described by reference to FIGS. 1 through 7.

It is apparent that various modifications and changes can be made without departing the spirit and scope of the present invention. The apparatus is constructed of materials substantially inert or nonreactive to the chemical or corrosive action of the fluid specimens to be measured and dispensed. The barrel of the syringe is normally constructed of glass, but can be constructed of a plastic or plastic-like material. The seals used in the instrument are normally constructed of plastic, and the rest of the syringe of various metals.

The seals are preferably formed of a rigid or semi-rigid, resilient form of plastic or plastic-like material. The self-lubricated plastics are especially preferred in this capacity, and can also be applied as a laminate or protective film. The polyfluorinated ethylene polymers, notable among which is polytetrafluoroethylene (Teflon), are particularly outstanding. Conventional resilient or elastic-like materials, such as natural or synthetic rubbers, can also be employed.

The plunger adjustment assembly, the needle of the syringe, the cylinder-piston units, and the like, are preferably constructed of metals, e.g., ferrous metals such as iron, iron alloys, steel, stainless steels, and the like; or such metals as aluminum, magnesium, brass, copper, bronze, chrome, alloys of these and other metals, and the like.

It is apparent that various changes, such as in the absolute or relative dimensions of the parts, materials used, and the like, as well as the suggested mode of withdrawing or delivering fluids, can be made without departing the spirit and scope of the invention, as will be apparent to those skilled in this art.

Having described the invention, what is claimed is:

1. In apparatus for repetitively accurately measuring and injecting preselected quantities of fluid specimens into a media such as an inlet to an analytical instrument, the combination comprising
    a housing, which can be mounted adjacent an inlet leading into the analytical instrument,
    a tubular member mounted within the housing, said tubular member including a pair of communicated openings therethrough, a first axial opening of the pair extending through the tubular member and housing, and a second opening adjacent to and communicated with said first axial opening which can be aligned upon the inlet leading into the analytical instrument,
    a needle syringe mounted upon the piston of a piston reciprocating unit, the needle of which is aligned upon said second opening through the tubular member within and through which the needle can be reciprocated by movement of the piston, said syringe including a barrel within which is mounted a plunger, said plunger constituting an integral portion of the piston reciprocating unit by virtue of which said plunger can be reciprocated within the chamber of said barrel,
    an injector feed assembly including a hollow probe provided with communicating upper and lower openings mounted on the piston of a piston reciprocating unit, said probe being aligned upon the said first axial opening through the tubular member within and through which the probe can be reciprocated by movement of the piston, and extended through the said first axial opening,
    means for transporting a fluid specimen contained in a vial, with a resilient, puncturable closure, below the said first axial opening and into the path of the hollow probe for penetration of said closure by the probe,
    means for pressurizing the fluid contents of the vial so that the fluid specimen contained within the vial can be transferred via the lower and upper side openings of the probe into the opening of the needle and into the barrel of the syringe,
    the improvement comprising
    a valved side inlet located within the barrel of the syringe forward of the point reached by the forward face of the plunger on movement to its maximum forward position within the syringe barrel, the valved side inlet providing, when the valve is in open position, a channel for flow of fluid from the dispensing end of the needle through the forward portion of the barrel, and rearward movement of the plunger to fill the barrel with a fluid specimen in predetermined quantity, and on subsequent forward thrust of the needle of the syringe into the inlet of the analytical instrument, with the valve in closed position the fluid specimen can be readily injected through the dispensing end of the needle by forward movement of the plunger.

2. The apparatus of claim 1 wherein the tubular member mounted within the housing and containing the pair of communicated openings is provided with means for pressurizing the fluid contents of the vial, this constituting fluid inlet means located above said second axial opening through the tubular member such that an upper opening within the hollow probe, which is fitted and traversable within the said first axial opening of the tubular member, and a lower probe opening are in communication via the opening through the hollow probe, and at such time the upper probe opening is located within said chamber opposite said fluid inlet means a pressurized fluid can be transmitted through the hollow probe to a vial to pressurize the fluid specimen contained therein for transfer via the probe to the needle opening and into the barrel of the syringe.

3. The apparatus of claim 1 wherein the piston reciprocating unit of the injector feed unit is a double-acting cylinder-piston unit comprising a barrel within which pressurized fluid can be admitted or expelled via inlet-outlet ports located on opposite sides of the area of traverse of an enlarged head affixed upon an end of the piston of the cylinder-piston unit, and the probe constitutes the piston of the piston reciprocating unit comprising a double-acting cylinder-piston unit that is directly affixed via one of its terminal ends to an enlarged head and reciprocable therewith when acted upon by ingress and egress of pressurized fluid admitted or expelled via inlet-outlet ports.

4. The apparatus of claim 1 wherein rearward of the barrel of said needle syringe there is provided an adjacent piston reciprocating unit inclusive of a piston which is the reciprocable element and also the plunger of the syringe.

5. The apparatus of claim 4 wherein the rearwardly located piston reciprocating unit is a double-acting cylinder piston unit, and the double-acting cylinder piston unit includes forward and rearward end walls which enclose an inner tubular wall forming a chamber within which the head portion of the plunger is contained, and forward and rearward inlet-outlet ports through which pressurized fluid can be admitted into the chamber to reciprocate the plunger.

6. The apparatus of claim 5 wherein the rearwardly located double-acting cylinder-piston unit includes an adjacent plunger adjustment assembly which limits the effective distance the plunger can travel within the barrel of the syringe.

7. The apparatus of claim 6 wherein the plunger adjustment assembly is comprised of a shaft adjustably extensible through the rearward wall of the chamber.

8. The apparatus of claim 5 wherein the rearwardly located double-acting cylinder-piston unit includes a plunger adjustment assembly comprising an internally threaded open end tubular member located within the rearward wall of the cylinder-piston unit, a shaft with an externally threaded head threadably engagable with the internal threads of said tubular member, an end of which shaft is extensible through an opening within the rearward wall of the chamber such that rotatable movement of the shaft in one direction extends the shaft into the chamber and rotatable movement in the other direction withdraws the shaft from the chamber, permitting presitting, thereby limiting and adjusting the effective distance the plunger can travel within the barrel of the syringe.

9. The apparatus of claim 8 wherein the shaft is fitted through a seal, and tubular retaining plug located within the rear wall of the chamber, the diameter of the externally threaded head of the shaft is larger than the diameter of the shaft, and the outer rearward face of the head is provided with a groove so that it can be easily rotated to facilitate presetting the effective distance that the plunger is free to travel within the barrel of the syringe.

10. The apparatus of claim 1 wherein the valved side inlet comprises a compartmented tubular member, a first compartment of which comprises a double acting cylinder piston unit, the reciprocable piston of which is slotted and the slotted portion thereof is extensible into a second compartment and within a lateral opening intersecting the axial opening through a tubular member mounted therein, said valved side inlet being adjoined and in communication with said axial opening of said tubular member, such that reciprocation of said double acting cylinder piston unit can align and misalign the axial opening and slotted end of said piston to open and close the valve.

11. The apparatus of claim 10 wherein the double-acting cylinder piston unit is spring biased such that the valve is in open position, the piston in said unit is provided with an enlarged head which mates with the inside wall of the tubular member constituting said first compartment, and said piston is actuatable by gas injected via gas inlet means into said compartment.

* * * * *